United States Patent
Bartra Sanmartí et al.

(10) Patent No.: US 9,056,864 B2
(45) Date of Patent: Jun. 16, 2015

(54) CRYSTALLINE FORM OF ABACAVIR THAT IS ESSENTIALLY FREE OF SOLVENT

(75) Inventors: Marti Bartra Sanmartí, Barcelona (ES); Ramón Berenguer Maimó, Barcelona (ES); Jordi Benet-Buchholz, Tarragona (ES); Lluis Solà I Carandell, Altafulla (ES)

(73) Assignee: ESTEVE QUIMICA, S.A., Barcelona (ES)

( * ) Notice: Subject to any disclaimer, the term of this patent is extended or adjusted under 35 U.S.C. 154(b) by 841 days.

(21) Appl. No.: 12/863,708

(22) PCT Filed: Jan. 21, 2009

(86) PCT No.: PCT/EP2009/050613
§ 371 (c)(1),
(2), (4) Date: Jul. 20, 2010

(87) PCT Pub. No.: WO2009/092716
PCT Pub. Date: Jul. 30, 2009

(65) Prior Publication Data
US 2010/0298354 A1    Nov. 25, 2010

Related U.S. Application Data

(60) Provisional application No. 61/038,441, filed on Mar. 21, 2008.

(30) Foreign Application Priority Data

Jan. 21, 2008   (EP) ..................................... 08382004

(51) Int. Cl.
A61K 31/52 (2006.01)
C07D 473/16 (2006.01)

(52) U.S. Cl.
CPC .................................... *C07D 473/16* (2013.01)

(58) Field of Classification Search
CPC .................................................. C07D 473/16
USPC ...................................... 544/277; 514/263.4
See application file for complete search history.

(56) References Cited

U.S. PATENT DOCUMENTS

| | | | |
|---|---|---|---|
| 5,034,394 A | 7/1991 | Daluge | |
| 5,981,500 A * | 11/1999 | Bishop et al. | 514/30 |
| 6,201,006 B1 * | 3/2001 | Koo et al. | 514/414 |
| 6,548,663 B1 * | 4/2003 | Cheesman et al. | 540/465 |
| 7,053,192 B2 * | 5/2006 | Li et al. | 536/7.4 |
| 7,067,529 B2 * | 6/2006 | Bolin et al. | 514/307 |
| 7,211,417 B2 * | 5/2007 | He et al. | 435/118 |
| 7,385,059 B2 * | 6/2008 | Berdini et al. | 546/188 |
| 7,557,209 B2 * | 7/2009 | Lawrence | 544/277 |
| 7,563,791 B2 * | 7/2009 | Dixon et al. | 514/243 |
| 7,585,882 B2 * | 9/2009 | Hopper et al. | 514/340 |
| 2002/0052513 A1 * | 5/2002 | Broadhurst et al. | 548/537 |
| 2003/0181498 A1 * | 9/2003 | Brittain et al. | 514/375 |
| 2005/0135999 A1 * | 6/2005 | Elomari et al. | 423/706 |
| 2007/0032435 A1 * | 2/2007 | Alani et al. | 514/18 |
| 2007/0249544 A1 * | 10/2007 | Himmelsbach et al. | 514/27 |
| 2008/0004448 A1 * | 1/2008 | Wayne et al. | 546/276.7 |
| 2008/0089835 A1 * | 4/2008 | Burton | 423/706 |
| 2008/0103186 A1 * | 5/2008 | Glover et al. | 514/395 |

(Continued)

FOREIGN PATENT DOCUMENTS

| | | |
|---|---|---|
| CN | 1763040 A * | 4/2006 |
| EP | 0434450 | 6/1991 |
| EP | 741710 | 11/1996 |
| EP | 1857458 A1 * | 11/2007 |
| JP | 8-92252 | 4/1996 |
| WO | 9852949 | 11/1998 |
| WO | 9921861 | 5/1999 |
| WO | 9939691 | 8/1999 |
| WO | 2008037760 | 4/2008 |
| WO | WO 2008074874 A1 * | 6/2008 |

OTHER PUBLICATIONS

Crimmins, J. Org. Chem. 1996, 61, 4192-4193.*
Konkel, Nucleosides & Nucleotides (1995), 14(9 & 10), 2061-77.*
Kim, Bulletin of the Korean Chemical Society (2007), 28(9), 1545-1548.*
Olivo, Journal of the Chemical Society, Perkin Transactions 1: Organic and Bio-Organic Chemistry (1998), (3), 391-392.*
Translation of CN1763040A (2006).*

(Continued)

*Primary Examiner* — Andrew D Kosar
*Assistant Examiner* — John S Kenyon
(74) *Attorney, Agent, or Firm* — Roberts Mlotkowski Safran & Cole, P.C.

(57) ABSTRACT

Crystalline form of abacavir that is essentially free of solvent of formula (I), in particular crystalline Form I, and its preparation process which comprises the following steps: a) crystallizing abacavir from a solution of said compound in a ($C_1$-$C_4$)-alcohol, dichloromethane, acetonitrile/water, or mixtures thereof; b) isolating the crystalline form of abacavir that appears in the prior step; and c) removing the solvent from the crystalline form of abacavir thus obtained. Crystalline Form I can also be obtained by dispersion of abacavir in acetonitrile. The crystalline form of abacavir that is essentially free of solvent is useful for the preparation of pharmaceutical compositions for use in the treatment and/or prophylaxis of HIV infections.

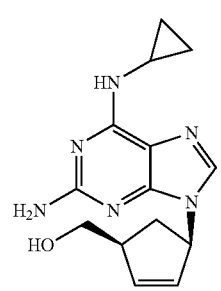

(I)

16 Claims, 3 Drawing Sheets

(56) References Cited

U.S. PATENT DOCUMENTS

| | | | |
|---|---|---|---|
| 2008/0139569 A1* | 6/2008 | Rocco et al. | 514/248 |
| 2008/0287471 A1* | 11/2008 | Fardis et al. | 514/263.37 |
| 2008/0319024 A1* | 12/2008 | Greil et al. | 514/342 |
| 2009/0069281 A1* | 3/2009 | Austad et al. | 514/183 |
| 2009/0124652 A1* | 5/2009 | Ach et al. | 514/293 |
| 2009/0137794 A1* | 5/2009 | Mendez et al. | 540/78 |
| 2009/0203705 A1* | 8/2009 | Biagetti et al. | 514/252.02 |
| 2009/0239946 A1* | 9/2009 | McKeown et al. | 514/494 |
| 2010/0021539 A1* | 1/2010 | Kowalski et al. | 424/464 |

OTHER PUBLICATIONS

"IR Spectroscopy of Solids" http://orgchem.colorado.edu/Technique/Procedures/IR/IRsolid.html downloaded from the internet Jan. 26, 2013.*

"Sampling Methods for IR Spectroscopy" http://www.pharmatutor.org/pharma-analysis/analytical-aspects-of-infra-red-spectroscopy-ir/ir-sampling-methods downloaded from the internet Jan. 26, 2013.*

"How to Prepare Samples for IR Spectroscopy" http://oldlaney.peralta.edu/Projects/30585/Chem_12A/Laboratory/Spectroscopy/IR_instr.pdf downloaded from the internet Jan. 26, 2013.*

"Truvada." © 2014. Available from: < http://www.truvada.com/ >.*

Mayo Clinic. "HIV/AIDS." © 2014. Available from: < http://www.mayoclinic.org/diseases-conditions/hiv-aids/basics/prevention/con-20013732?p=1 >.*

S. Daluige et al., "An Efficient, Scalable Synthesis of the HIV Reverse Transcriptase Inhibitor Ziagen (1592U89)" Nucleosides, nucleotides and nucleic acids 2000, vol. 19, pp. 297-327.

International Search Report and Written Opinion of the International Searching Authority for PCT/EP2009/050613 mailed Apr. 27, 2009.

International Conference on Harmonisation of Technical Requirements for registration of pharmaceuticals for human use ICH Harmonised Tripartite Guideline Impurities: Guideline for Residual Solvents Q3C (R5) Current Step 4 version dated Feb. 4, 2011.

Chemical Biological and Industrial Applications of Infrared Spectroscopy by James R. Durig, Department of Chemistry Univeristy of South Carolina Columbia, South Carolina 29208 A Wiley-Interscience Publication 1985, by John Wiley & Sons Ltd., pp. 52-53.

Vogel's Textbook of Practical Organic Chemistry 4th edition Longman Group Limited 1978.

* cited by examiner

CRYSTALLINE FORM OF ABACAVIR THAT IS ESSENTIALLY FREE OF SOLVENT

CROSS REFERENCE TO RELATED APPLICATIONS

The present Application is a U.S. national phase of PCT/EP2009/050613 filed on Jan. 21, 2009 ("PCT Application"), which claims priority from European Application No. 08382004.3 filed on Jan. 21, 2008 and U.S. Provisional Application No. 61/038,441, filed on Mar. 21, 2008 all of which are hereby incorporated by reference in their entirety into the present Application. Hence this Application claims the benefit of priority of European patent application EP08382004.3 filed on 21 Jan. 2008 and U.S. Provisional Patent Application U.S. 61/038,441 filed on 21 Mar. 2008.

The present invention relates to a crystalline form of abacavir base, a process for its preparation, its use as therapeutically active ingredient, and pharmaceutical compositions comprising it.

BACKGROUND ART

Abacavir is the International Nonproprietary Name (INN) of {(1S,4R)-4-[2-amino-6-(cyclopropylamino)-9H-purin-9-yl]-cyclopent-2-enyl}methanol and CAS No. 136470-78-5. Abacavir and therapeutically acceptable salts thereof, in particular the hemisulfate salt, are well-known as potent selective inhibitors of HIV-1 and HIV-2, and can be used in the treatment of human immunodeficiency virus (HIV) infection.

The structure of abacavir corresponds to formula (I):

(I)

EP 434450-A discloses certain 9-substituted-2-aminopurines including abacavir and its salts, methods for their preparation, and pharmaceutical compositions using these compounds.

Different preparation processes of abacavir are known in the art. In some of them abacavir is obtained starting from an appropriate pyrimidine compound, coupling it with a sugar analogue residue, followed by a cyclisation to form the imidazole ring and a final introduction of the cyclopropylamino group at the 6 position of the purine ring.

According to the teachings of EP 434450-A, the abacavir base is finally isolated by trituration using acetonitrile (ACN) or by chromatography, and subsequently it can be transformed to a salt of abacavir by reaction with the corresponding acid. Such isolation methods (trituration and chromatography) usually are limited to laboratory scale because they are not appropriate for industrial use. Furthermore, the isolation of the abacavir base by trituration using acetonitrile gives a gummy solid (Example 7) and the isolation by chromatography (eluted from methanol/ethyl acetate) yields a solid foam (Example 19 or 28).

Other documents also describe the isolation of abacavir by trituration or chromatography, but always a gummy solid or solid foam is obtained (cf. WO 9921861 and EP 741710-A), which would be difficult to operate on industrial scale.

WO 9852949 describes the preparation of abacavir which is isolated from acetone. According to this document the manufacture of the abacavir free base produces an amorphous solid which traps solvents and is, therefore, unsuitable for large scale purification, or for formulation, without additional purification procedures (cf. page 1 of WO 9852949). Other documents also describe the obtention of abacavir from acetone (cf. Susan M. Daluge et al., *Nucleosides, nucleotides and nucleic acids* 2000, vol. 19, pp. 297-327; WO 9939691 or WO 2008037760). In the last one the preparation of abacavir from ethyl acetate is also described. In some of these documents it is mentioned that the abacavir obtained is a solid but nothing is said about the fact that the compound obtained could be amorphous or could trap solvent in its lattice. The reproduction of the preparation of abacavir from acetone showed that an acetone solvate of abacavir is obtained, which is in agreement with WO 9852949 regarding to the fact that the product traps solvent. The crystallization of abacavir from ethyl acetate as described in WO 2008037760 showed that an ethyl acetate solvate of abacavir is obtained which spontaneously changed to give a brown gum after few hours.

It is not acceptable to formulate pharmaceuticals containing substantial amounts of organic solvent due to potential solvent toxicity to the recipient thereof and changes in potency of the pharmaceutical as a function of the solvent.

In WO 9852949 the use of a salt of abacavir is proposed, in particular the hemisulfate salt which shows improved physical properties regarding to the abacavir base known in the art. Said properties allow the manufacture of the salt on industrial scale, and in particular its use for the preparation of pharmaceutical formulations. However, the preparation of a salt of abacavir involves an extra processing step of preparing the salt, increasing the cost and the time to manufacture the compound. Generally, the abacavir free base is the precursor compound for the preparation of the salt. Thus, depending on the preparation process used for the preparation of the salt, the isolation step of the abacavir free base must also be done.

Thus, there is still a need to find new solid forms of abacavir base suitable to operate on industrial scale, either to be used directly as pharmaceutical active ingredient in a pharmaceutical formulation, or if desired, to be subsequently transformed into a pharmaceutically acceptable salt thereof.

Furthermore, the different solid forms of a pharmaceutically active ingredient can have different characteristics, and offer certain advantages, in methods of manufacture and also in pharmacology. Thus, the discovery of new solid forms can contribute to clear improvements in the efficiency of methods of production and/or improvements in the characteristics of the pharmaceutical formulations of the active ingredients, since some forms are more adequate for one type of formulation, and other forms for other different formulations.

SUMMARY OF THE INVENTION

The inventors have found a crystalline form of abacavir that is essentially free of solvent, with improved physical characteristics, thereby solving some of the problems previously mentioned. To our knowledge, it is the first crystalline form of abacavir base that is essentially free of solvent. In particular the inventors have found a crystalline form, named Form I, which is essentially free of solvent, stable, easy to handle, and a process to prepare it that is reproducible. This novel form does not trap solvent. Solid forms of abacavir which trap solvent are known in the art, in particular forms containing acetone or ethyl acetate, but the amount of acetone or ethyl acetate present in the corresponding solid forms of abacavir are unacceptable for its use in pharmacy. Additionally, as it is illustrated in Comparative Example 1, the ethyl acetate solvate of abacavir is not stable at room temperature.

Furthermore, the improved physical characteristics of the crystalline form of abacavir that is essentially free of solvent, compared with the abacavir described in EP 434450-A, WO 9921861, and in EP 741710-A which is a gummy solid or a solid foam, provide improved processing characteristics and the provision of a compound suitable for use in the preparation of pharmaceutical formulations.

Therefore, it is a significant contribution to the art to provide a new crystalline form of abacavir which does not trap solvent and has the ability to crystallize and to filter easily, methods for its preparation, its use as a therapeutically active agent and pharmaceutical compositions comprising it.

For the avoidance of doubt, as used herein the term abacavir, abacavir base, or abacavir free base is used indistinctly to address to the compound {(1S,4R)-4-[2-amino-6-(cyclopropylamino)-9H-purin-9-yl]-cyclopent-2-enyl} methanol of formula (I) below.

Thus, according to one aspect of the present invention, it is provided a crystalline form of abacavir that is essentially free of solvent of formula (I).

(I)

A crystalline form of abacavir that is essentially free of solvent of formula (I) characterized by having a powder X-ray diffractogram that comprises characteristic peaks at approximately 8.0, 10.0, 10.2, 10.6, 11.9, 12.4, 12.7, 15.0, 16.1, 16.6, 19.5, 20.2, 20.6, 20.7, 21.9, 23.0, 23.9, and 25.0 degrees 2 theta is also provided. This new crystalline form is named Form I.

Another aspect of the present invention relates to a process for the preparation of the crystalline Form I of abacavir as defined above, characterized by comprising the following steps: a) crystallizing abacavir from a solution of said compound in a solvent system selected from the group consisting of $(C_1-C_4)$-alcohol, dichloromethane, acetonitrile/water, and mixtures thereof; b) isolating the crystalline form of abacavir base that appears in the prior step; and c) removing the solvent from the crystalline form of abacavir thus obtained. Alternatively, the crystalline Form I of abacavir of the present invention can be obtained by a preparation process comprising the dispersion of abacavir in acetonitrile at a temperature comprised between 30-40° C. during the necessary period of time for the conversion of the starting abacavir into the crystalline Form I of the present invention. Generally, it is dispersed at least 30'.

Another aspect of the present invention relates to a pharmaceutical composition that comprises as active ingredient a therapeutically effective amount of the crystalline form of abacavir that is essentially free of solvent as defined above, together with appropriate pharmaceutically acceptable excipients or carriers.

Finally, another aspect of the present invention relates to the use of the crystalline form of abacavir that is essentially free of solvent as defined above for the preparation of a medicament for the treatment and/or prophylaxis of HIV infections. This aspect can also be formulated as crystalline form of abacavir that is essentially free of solvent as defined above for use in the treatment and/or prophylaxis of HIV infections.

The invention is also related to a method of treatment and/or prophylaxis of a mammal, including a human, suffering from or being susceptible to HIV infections, said method comprising the administration to said patient of a therapeutically effective amount of the crystalline form of abacavir that is essentially free of solvent of the present invention, together with pharmaceutically acceptable excipients or carriers.

DETAILED DESCRIPTION OF THE INVENTION

Figure 1:
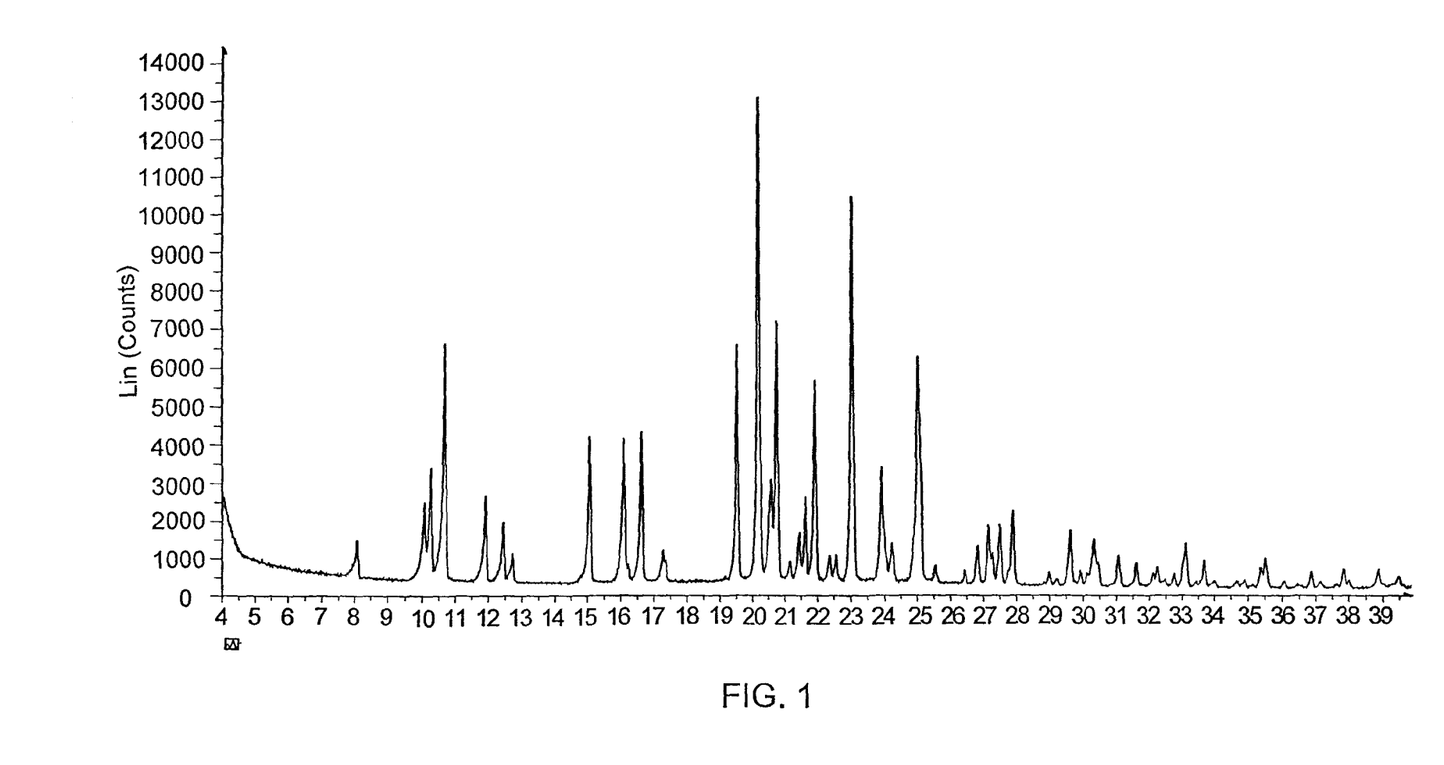
FIG. 1 shows the powder X-ray diffraction (PXRD) pattern of the crystalline Form I of abacavir of the present invention that is essentially free of solvent.

In a particular embodiment, the new crystalline form of abacavir that is essentially free of solvent is Form I, characterized by exhibiting in the powder X-ray diffractogram a pattern of peaks, expressed in 2 theta units in degrees, $2\theta$ (°), and in d-values in Angstrom, d (Å), which is shown in Table 1 and FIG. 1.

TABLE 1

| d (Å) | 2θ (°) | Relative intensity (%) |
|---|---|---|
| 11.02 | 8.0 | 11 |
| 8.82 | 10.0 | 19 |
| 8.65 | 10.2 | 26 |
| 8.30 | 10.6 | 51 |
| 7.45 | 11.9 | 20 |
| 7.14 | 12.4 | 15 |
| 6.98 | 12.7 | 8 |
| 5.89 | 15.0 | 32 |
| 5.51 | 16.1 | 32 |
| 5.47 | 16.2 | 6 |
| 5.34 | 16.6 | 33 |
| 5.14 | 17.2 | 9 |
| 5.12 | 17.3 | 7 |
| 4.55 | 19.5 | 50 |
| 4.40 | 20.2 | 100 |
| 4.32 | 20.6 | 24 |
| 4.28 | 20.7 | 55 |
| 4.20 | 21.1 | 7 |
| 4.15 | 21.4 | 13 |
| 4.11 | 21.6 | 20 |
| 4.05 | 21.9 | 43 |
| 3.97 | 22.4 | 8 |
| 3.94 | 22.5 | 8 |
| 3.86 | 23.0 | 80 |
| 3.72 | 23.9 | 26 |
| 3.67 | 24.2 | 11 |
| 3.58 | 24.9 | 12 |
| 3.55 | 25.0 | 48 |

TABLE 1-continued

| d (Å) | 2θ (°) | Relative intensity (%) |
|---|---|---|
| 3.48 | 25.5 | 6 |
| 3.37 | 26.4 | 5 |
| 3.32 | 26.8 | 10 |
| 3.28 | 27.2 | 14 |

The PXRD is obtained using the diffractometer disclosed below applying $Cu_{K\alpha 1}$ radiation ($\lambda$=1.54060 Å). In order to acquire a powder diffraction pattern of the solid, approximately 20 mg of the non manipulated samples were prepared in standard sample holders using two foils of polyacetate. Powder diffraction patterns were acquired on a D8 Advance Series 2 theta/theta powder diffraction system using $Cu_{K\alpha 1}$ radiation in transmission geometry. The system is equipped with a VANTEC-1 single photon counting PSD, a Germanium monochromator, a ninety positions auto changer sample stage, fixed divergence slits and radial soller. Programs used: data collection with DIFFRAC plus XRD Commander V 2.5.1 and evaluation with EVA V.12.0.

Figure 3:
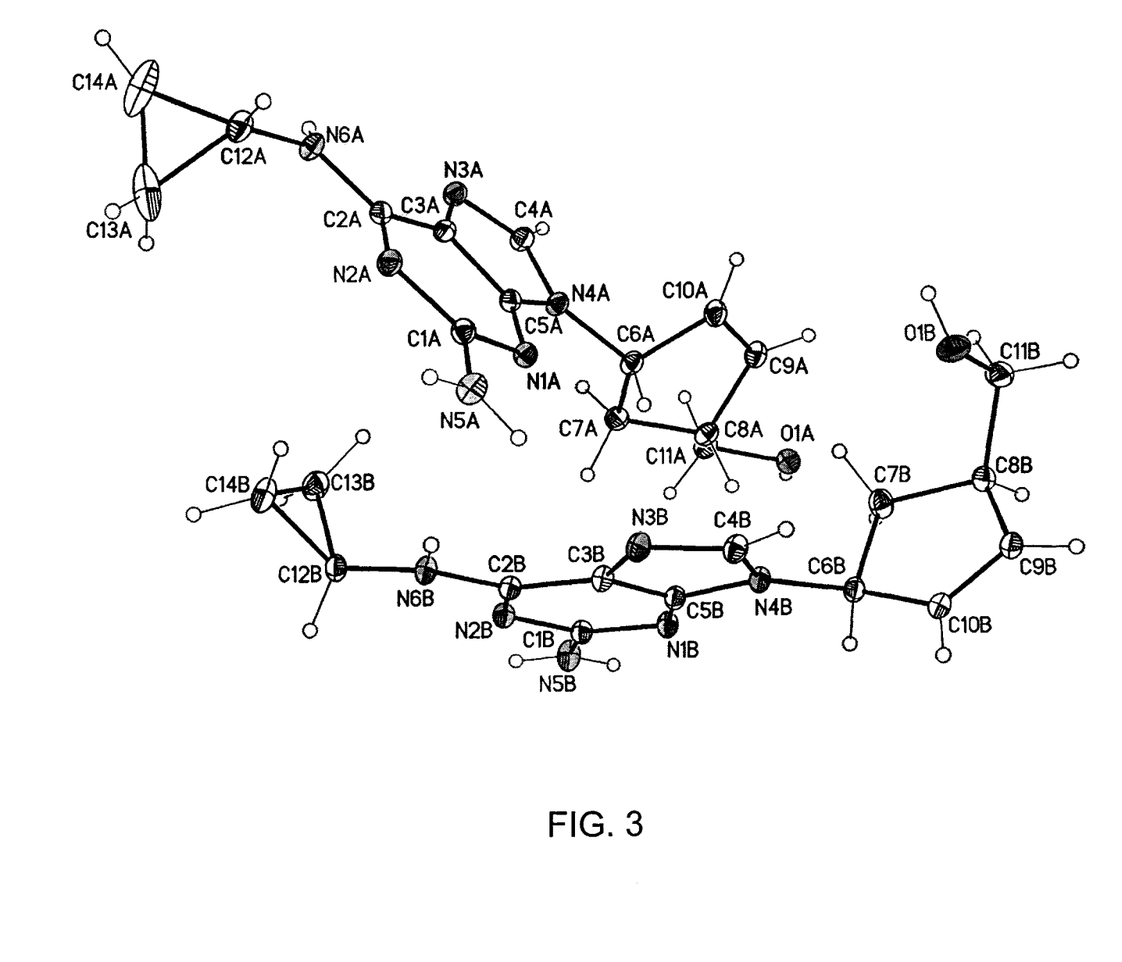
FIG. 3 shows the Ortep-Plot (50%) of abacavir Form I with labeling scheme of the independent molecules in the unit cell.

This new crystalline Form I of abacavir exhibits the following data of the monocrystal cell obtained by single crystal X-ray diffraction (SCXRD):
Crystal system Monoclinic
Space group $P2_1$
Unit cell dimensions:
a=9.1975(5) Å α=90°.
b=13.7033(7) Å β=109.096(3)°.
c=11.6018(5) Å γ=90°.
Volume=1381.78 (12 Å$^3$)
Density=1.376 Mg/m$^3$ The representation of the disposition of the two independent molecules present in the elementary cell is shown in FIG. 3.

The measured crystal was selected using a Zeiss stereomicroscope using polarized light and prepared under inert conditions immersed in perfluoropolyether as protecting oil for manipulation. Crystal structure determination was carried out using a Bruker-Nonius diffractometer equipped with a APPEX 2 4K CCD area detector, a FR591 rotating anode with $Mo_{K\alpha}$ radiation, Montel mirrors as monochromator and a Kryoflex low temperature device (T=100 K). Fullsphere data collection omega and phi scans. Programs used: Data collection Apex2 V.1.0-22 (Bruker-Nonius 2004), data reduction Saint+Version 6.22 (Bruker-Nonius 2001) and absorption correction SADABS V. 2.10 (2003). Crystal structure solution was achieved using direct methods as implemented in SHELXTL Version 6.10 (Sheldrick, Universität Göttingen (Germany), 2000) and visualized using XP program. Missing atoms were subsequently located from difference Fourier synthesis and added to the atom list. Least-squares refinement on $F_O^2$ using all measured intensities was carried out using the program SHELXTL Version 6.10 (Sheldrick, Universität Göttingen (Germany), 2000). All non hydrogen atoms were refined including anisotropic displacement parameters.

These new data confirm that the new crystalline form does not contain solvent in its crystalline structure, therefore it is not a solvate.

A calculation of the ideal powder diffraction pattern from the single crystal data was in agreement with that shown in FIG. 1.

Thus, this form is essentially free of solvent, and is free of solvation. By the expression "essentially free of solvent" it is understood that it complies with the relevant pharmaceutical specifications for the presence of solvents. By free solvent it is understood that the solvent does not form part of the product's crystalline structure, and by solvation solvent it is understood that the solvent is incorporated into the product's crystalline structure.

Figure 2:
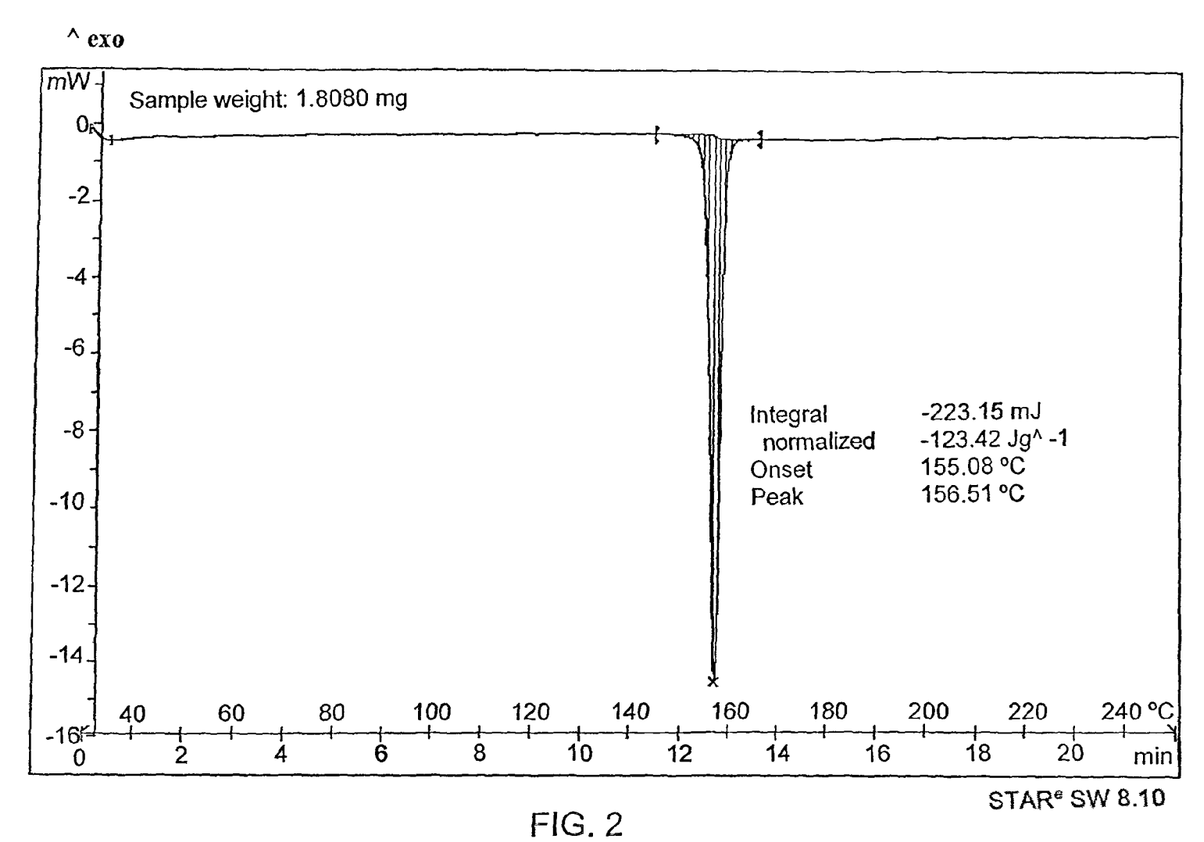
FIG. 2 shows the Differential Scanning Calorimetry (DSC) curve of the crystalline Form I of abacavir of the present invention that is essentially free of solvent.

The crystalline Form I of abacavir is also characterized by DSC, showing a melting peak at approximately 157° C. (cf. FIG. 2).

DSC analyses were recorded in a Mettler Toledo DSC822e. Samples of 1-2 mg were weighted into 40 μL aluminium crucibles with a pinhole lid, and were heated, under nitrogen (50 mL/Min), from 30 to 250° C. at a heating rate of 10° C./min. Data collection and evaluation was done with software STARe.

As mentioned above, the crystalline Form I of abacavir of the present invention can be prepared by a process comprising the following steps: a) crystallizing abacavir from a solution of said compound in a solvent system selected from the group consisting of ($C_1$-$C_4$)-alcohol, dichloromethane, acetonitrile/water, and mixtures thereof; b) isolating the crystalline form of abacavir that appears in the prior step; and c) removing the solvent from the crystalline form of abacavir thus obtained.

In a preferred embodiment, the solvent system is a ($C_1$-$C_4$)-alcohol. Examples of ($C_1$-$C_4$)-alcohols include methanol, ethanol, n-propanol, isopropanol, n-butanol, tert-butanol, sec-butanol, and isobutanol. Preferably, the ($C_1$-$C_4$)-alcohol is selected from methanol, ethanol, and isopropanol.

In another preferred embodiment, the preparation process further comprises adding an antisolvent to the solution of abacavir in a ($C_1$-$C_4$)-alcohol. Preferably the antisolvent is a ($C_5$-$C_8$)-alkane such as cyclohexane, heptane, pentane and hexane. In a more preferred embodiment n-pentane is added to the solution of abacavir in a ($C_1$-$C_4$)-alcohol.

Generally, the starting abacavir is dissolved at a temperature near or at the boiling point of the solvent employed. Then, the hot solution is slowly cooled, optionally an antisolvent can be added, causing the dissolved abacavir to crystallize out and the resulting suspension is kept at that temperature during a specified time, generally overnight, with stirring. The resulting suspension is easily stirred.

The separation of the product from the supernatant solution can be done by a conventional method such as filtration. The solid filters readily thereby making easy the preparation.

The remaining solvent can be removed from the product by drying, optionally under vacuum. The product is also easily dried since it does not occlude solvent into its crystalline structure.

Thus, the physical properties of the crystalline Form I of abacavir of the present invention allow for easy manipulation during all the preparation process. Furthermore the process is reproducible and robust and therefore easily industrializable.

The crystalline Form I of abacavir is obtained with high yields and high purity that is greater than 99%. Likewise, it is obtained with an elevated optical purity, that is, with an enantiomeric excess (e.e.) equal to or greater than 99%.

Alternatively, the crystalline Form I of abacavir can be obtained by a preparation process comprising the dispersion of abacavir in acetonitrile at a temperature comprised between 20-50° C. during the necessary period of time for the conversion being completed. Generally, it is dispersed at least 30'. In a preferred embodiment the dispersion of abacavir in acetonitrile is carried out at a temperature comprised between 30-40° C.

The new crystalline form of the present invention that is essentially free of solvent, can be converted into a pharmaceutically acceptable salt by methods known in the art, for instance, by reaction with the corresponding pharmaceutically acceptable acid in an appropriate solvent or by ions exchange between a salt of abacavir and an inorganic or organic salt. Preferably, the pharmaceutically acceptable salt is the hemisulfate salt.

The most adequate conditions for carrying out said processes vary depending on the parameters considered by the expert in the art, such as, for example, the concentration of the starting material, temperature, and the like. These can be easily determined by said skilled person in the art by routine tests and with the help of the teachings of the examples given in this description.

The pharmaceutical composition of the present invention comprises a therapeutically effective amount of the crystalline form of abacavir that is essentially free of solvent, together with suitable pharmaceutically acceptable excipients or carriers. The compound of the present invention can be normally formulated in accordance with standard pharmaceutical practice.

The crystalline form of abacavir that is essentially free of solvent of the present invention is useful in the treatment and/or prophylaxis of HIV infections.

Throughout the description and the claims the word "comprises" and its variants are not meant to exclude other technical characteristics, additives, components or steps. For skilled persons in the art, other objects, advantages and characteristics of the invention can be deduced in part from the description and partly from the practice of the invention. The following examples are provided for illustrative means, and are not meant to be limiting of the present invention.

EXAMPLES

Example 1

Preparation of Crystalline Form I of Abacavir Base Using Methanol as Solvent

Abacavir (1.00 g, containing about 17% of dichloromethane) was dissolved in methanol (2.2 mL) at reflux. The solution was slowly cooled to −5° C. and the resulting suspension was kept at that temperature overnight under gentle stirring. The mixture was filtered off and dried under vacuum (7-10 mbar) at 40° C. for 4 hours to give a white solid (0.55 g, 66% yield, <5000 ppm of methanol). The PXRD analysis gave the diffractogram shown in FIG. 1.

Example 2

Preparation of Crystalline Form I of Abacavir Base Using Ethanol as Solvent

Abacavir (1.00 g, containing about 17% of dichloromethane) was dissolved in ethanol (3.5 mL) at reflux. The solution was slowly cooled to −5° C. and, the resulting suspension, was kept at that temperature overnight under gentle stirring. The mixture was filtered off and dried under vacuum (7-10 mbar) at 40° C. for 4 hours to give a white solid (0.63 g, 76% yield, <5000 ppm of ethanol). The PXRD analysis gave the diffractogram shown in FIG. 1.

Example 3

Preparation of Crystalline Form I of Abacavir Base Using Isopropanol as Solvent

Abacavir (1.00 g, containing about 17% of dichloromethane) was dissolved in isopropanol (5.5 mL) at reflux. The solution was slowly cooled to −5° C. and, the resulting suspension, was kept at that temperature overnight under gentle stirring. The mixture was filtered off and dried under vacuum (7-10 mbar) at 40° C. for 4 hours to give a white solid (0.67 g, 81% yield, <5000 ppm of isopropanol). The PXRD analysis gave the diffractogram shown in FIG. 1.

Example 4

Recrystallization of crystalline Form I of abacavir base using Isopropanol as Solvent Crystalline Form I of abacavir (6.71 g) was dissolved in isopropanol (30 mL) at reflux. The solution was slowly cooled to −5° C. and, the resulting suspension, was kept at that temperature overnight under gentle stirring. The mixture was filtered off and dried under vacuum (7-10 mbar) at 40° C. for 4 hours to give a white solid (6.05 g, 90% yield, <5000 ppm of isopropanol). The PXRD analysis gave the diffractogram shown in FIG. 1.

Example 5

Preparation of Crystalline Form I of Abacavir Base in ACN/$H_2O$

General procedure: Abacavir (400-500 mg, containing about 17% of dichloromethane) was dissolved in the minimum amount of ACN and water mixture (Table 2) at 60° C. The resulting solution was cooled to room temperature (RT), and crystals were collected by filtration and dried under vacuum (5-10 mbar) at 40° C. for 4 h.

The crystallization conditions are summarized in Table 2:

TABLE 2

| Example | Solvent system | Solvent volume (mL) | Residual solvent |
|---|---|---|---|
| 5a | ACN/$H_2O$ 9:1 | 2.8 | 0.5% |
| 5b | ACN/$H_2O$ 85:15 | 1.2 | 0.5% |
| 5c | ACN/$H_2O$ 7:3 | 0.4 | 0.2% |

In all the experiments above crystalline Form I of abacavir base was obtained. The residual solvent content was determined by $^1$H-NMR. The crystalline form obtained was essentially free of solvent.

Example 6

Preparation of Crystalline Form I of Abacavir Base by Crystallization by Antisolvent Addition General procedure: abacavir (200-500 mg, containing about 17% dichloromethane) was dissolved in the minimum amount of solvent at 35° C. Then, n-pentane was added to the solution until crystallization was observed, the resulting suspension was cooled to room temperature and the solid was filtered and dried under vacuum (5-10 mbar) at 40° C. for 4 h.

The crystallization conditions are summarized in Table 3:

TABLE 3

| Example | Solvent | Antisolvent (mL) | Residual solvent |
|---|---|---|---|
| 6a | Methanol 0.2 mL | n-pentane 0.5 mL | 0.1% |
| 6b | Ethanol 0.5 mL | n-pentane 1 mL | 0.5% |

In both experiments above crystalline Form I of abacavir was obtained. The residual solvent content was determined by $^1$H-NMR. The crystalline form obtained was essentially free of solvent.

Example 7

Preparation of Crystalline Form I of Abacavir Base by Dispersion in Acetonitrile Abacavir (200-500 mg, containing about 17% dichloromethane) was dispersed in 11 mL of acetonitrile at 35° C. The resulting suspension was maintained to said temperature during at least 30', then the dispersion was cooled to room temperature and the solid was filtered and dried under vacuum (5-10 mbar) at 40° C. for 4 h. Crystalline Form I of abacavir base was obtained. The solvent content was determined by $^1$H-NMR. Residual solvent: 0.2%. The crystalline form obtained was essentially free of solvent.

COMPARATIVE EXAMPLE 1

Crystallization of Abacavir in Ethyl Acetate

Abacavir (1.5 g) was heated in ethyl acetate (30 mL) to reflux and the resultant solution was cooled to 0/5° C. The resulting slurry was filtered off and the obtained solid was dried under vacuum at 40° C. until constant weight. There was obtained 1.2 g (67% yield) of abacavir solvate as a white solid containing about 16% of ethyl acetate. The PXRD analysis gave a different diffractogram from the one shown in FIG. 1. The solvent content was determined by $^1$H-NMR. Few hours later, this solid spontaneously changed to give a brown gum. That means that the compound obtained is unstable as a solid.

COMPARATIVE EXAMPLE 2

Crystallization of Abacavir in Acetone
(Reproduction of Example 4 of WO 9939691)

A solution of abacavir (2.54 g) in ethanol was concentrated by distillation under reduced pressure to dryness. Acetone (120 mL) was added and the mixture was re-concentrated to give a fluid volume of about 11 mL. The resultant suspension was cooled to 0/5° C. and the solid was filtered and dried in vacuum at room temperature until constant weight to give 2.40 g of abacavir solvate (86% yield) containing about 9.4% of acetone. The PXRD analysis gave a different diffractogram from the one shown in FIG. 1. The solvent content was determined by $^1$H-NMR.

The invention claimed is:

1. The crystalline form of abacavir of formula (I) that comprises equal to or less than 5000 ppm of solvent and is free of solvation, characterized by having a powder X-ray diffractogram that comprises characteristic peaks at 8.0, 10.0, 10.2, 10.6, 11.9, 12.4, 12.7, 15.0, 16.1, 16.6, 19.5, 20.2, 20.6, 20.7, 21.9, 23.0, 23.9, and 25.0 degrees 2 theta at a Cu$_{K\alpha 1}$ radiation ($\lambda$=1.54060Å)

2. The crystalline form of abacavir according to claim 1, further characterized by a powder X-ray diffractogram as in FIG. 1.

3. A preparation process of the crystalline form of abacavir as defined in claim 1, comprising the following steps:
   a) crystallizing abacavir from a solution of abacavir in a solvent system selected from the group consisting of (C$_1$-C$_4$)-alcohol, dichloromethane, acetonitrile/water, and mixtures thereof; wherein the crystallization of step a) is carried out by cooling the solution to crystallize out the abacavir;
   b) isolating the crystalline form of abacavir that appears in the prior step; and
   c) removing the solvent from the crystalline form of abacavir thus obtained.

4. The preparation process according to claim 3, wherein the solvent system is a (C$_1$-C$_4$)-alcohol, which is selected from the group consisting of: methanol, ethanol, and isopropanol.

5. A preparation process of the crystalline form of abacavir as defined in claim 1, comprising dispersing abacavir in acetonitrile at a temperature between 20-50° C. for a period of time sufficient to convert starting abacavir to the crystalline form of claim 2, and then isolating the abacavir from the acetonitrile.

6. The preparation process according to claim 5, wherein the dispersion of abacavir in acetonitrile is carried out at a temperature between 30-40° C.

7. The preparation process according to claim 3, further comprising d) converting the abacavir into a pharmaceutically acceptable salt by reaction of abacavir with a pharmaceutically acceptable acid.

8. The preparation process according to claim 5, further comprising converting the abacavir into a pharmaceutically acceptable salt by reaction of abacavir with a pharmaceutically acceptable acid.

9. A pharmaceutical composition comprising a crystalline form of abacavir as defined in claim 1, together with pharmaceutical excipients or carriers.

10. A method of treatment of a mammal, suffering from HIV infections, said method comprising the administration to said mammal of a therapeutically effective amount of a crystalline form of abacavir as defined in claim 1, together with pharmaceutically acceptable excipients or carriers.

11. The method according to claim 10, wherein said mammal is a human patient.

12. A preparation process of the crystalline form of abacavir as defined in claim 1 or claim 2, comprises the following steps:
   a) providing a solution of abacavir in a solvent comprising a (C$_1$-C$_4$)-alcohol;
   b) adding a (C$_5$-C$_8$)-alkane as an antisolvent to the solution of abacavir in a solvent comprising a (C$_1$-C$_4$)-alcohol;

c) isolating the crystalline form of abacavir that appears in step b); and
d) removing the solvent from the crystalline form of abacavir thus obtained.

13. The preparation process according to claims 12, wherein the alkane is n-pentane.

14. The process according to claim 12, wherein the ($C_1$-$C_4$)-alcohol is selected from the group consisting of methanol, ethanol, and isopropanol.

15. A preparation process of the crystalline form of abacavir as defined in claim 1 or claim 2 comprising the following steps:
   a) providing a solution of abacavir in a solvent comprising an alcohol selected from the group consisting of methanol or ethanol;
   b) adding n-pentane as an antisolvent to the solution of abacavir in the solvent;
   c) isolating the crystalline form of abacavir that appears in step b); and
   d) removing the solvent from the crystalline form of abacavir thus obtained.

16. The preparation process according to claim 5, wherein the period of time is about 30 minutes.

\* \* \* \* \*